United States Patent [19]
Clostermann

[11] Patent Number: 5,286,195
[45] Date of Patent: Feb. 15, 1994

[54] SCREW ELEMENT FOR THREADEDLY CONNECTING A MULTI-PART DENTAL PROSTHESIS

[75] Inventor: Volkhard-Hagen Clostermann, Hagen, Fed. Rep. of Germany

[73] Assignee: ZL Microdent-Attachment GmbH, Breckerfeld, Fed. Rep. of Germany

[21] Appl. No.: 741,397

[22] PCT Filed: Nov. 10, 1990

[86] PCT No.: PCT/DE90/00851
§ 371 Date: Oct. 30, 1991
§ 102(e) Date: Oct. 30, 1991

[87] PCT Pub. No.: WO91/08713
PCT Pub. Date: Jun. 27, 1991

[30] Foreign Application Priority Data
Dec. 7, 1989 [DE] Fed. Rep. of Germany ... 8914415[U]

[51] Int. Cl.⁵ ............ A61C 13/12; A61C 13/225; A61C 8/00
[52] U.S. Cl. .................................... 433/172; 433/173
[58] Field of Search .................. 433/172, 173, 174

[56] References Cited
U.S. PATENT DOCUMENTS

| | | | |
|---|---|---|---|
| 4,631,031 | 12/1986 | Richter | 433/173 |
| 4,713,003 | 12/1987 | Symington et al. | 433/173 |
| 4,832,601 | 5/1989 | Linden | 433/173 |
| 4,842,518 | 6/1989 | Linkow et al. | |
| 4,854,872 | 8/1989 | Detsch | |
| 4,872,839 | 10/1989 | Brajnovic | |
| 4,932,868 | 6/1990 | Linkow et al. | |
| 4,938,693 | 7/1990 | Bulakiev | |
| 5,152,687 | 10/1992 | Amino | 433/174 X |
| 5,169,308 | 12/1992 | Kvist | 433/172 X |
| 5,213,502 | 5/1993 | Daftary | 433/172 |

Primary Examiner—John J. Wilson
Assistant Examiner—Nicholas D. Lucchesi
Attorney, Agent, or Firm—Spencer, Frank & Schneider

[57] ABSTRACT

The screw element is composed of a threaded sleeve (1), a locknut (2) and a cone screw (3). The threaded sleeve (1) has an edge (12) and following the edge (12) a portion (14) that is free of threads; the cone screw (3) has a head (35), a threaded shaft (36) and, between head (35) and threaded shaft (36), a portion (33) that is free of threads; the locknut (2) has an internal cone (22) whose portion having the smallest diameter is provided with an internal thread (23) that is adapted to the threaded shaft (36) of the cone screw (3). The threaded sleeve (36) of the cone screw (3) is screwed into the threaded shaft (1) and its head (35) is supported in the internal cone (22).

1 Claim, 2 Drawing Sheets

SCREW ELEMENT FOR THREADEDLY CONNECTING A MULTI-PART DENTAL PROSTHESIS

TECHNICAL FIELD

The invention relates to a screw element for screwing together a multi-part dental prosthesis, with the screw element including a threaded sleeve, a locknut lying against the edge of the threaded sleeve and a cone screw whose threaded shaft is screwed into the threaded sleeve and whose head is supported in an interior cone of the locknut.

STATED OF THE ART

Screw elements composed of two or more individual components are employed to screw together multi-part dental prostheses, for example divided bridges and implant superstructures. Screw elements of this type are composed of a threaded sleeve, a locknut and a cone screw. The threaded sleeve as well as the threaded shaft of the cone screw are provided with a thread over their entire length The locknut has a cylindrical exterior surface and a conical interior surface, but no thread. The prior art screw elements have the following drawbacks: the dentist intending to screw together the components of the multi-part dental prosthesis, for example the bridge elements, in the mouth of his patient by means of the cone screw encounters the difficulty of reliably introducing the cone screw, which has a small diameter, into the threaded sleeve. In everyday practice it happens that the patient swallows the screw.

DESCRIPTION OF THE INVENTION

This is where the invention intends to come to the aid. It is the object of the invention to configure a screw element of this type so that the cone screw can be connected with the locknut and is held captive in it without interfering with the function of the screw element. According to the invention, this is accomplished in that the threaded sleeve, following its edge, and the cone screw, between its head and its threaded shaft, are each provided with a portion that is free of threads and, in the region in which its interior cone has the smallest diameter, the locknut is provided with an internal thread that is adapted to the threaded shaft of the cone screw.

In contrast to the prior art locknuts, the locknut of the invention is provided with an internal thread on its interior cone, in the region where it has the smallest diameter, into which the threaded shaft of the cone screw can be screwed. Only at the end opposite its head is the threaded shaft of the cone screw is provided with an external thread that can be screwed into the internal thread of the locknut. This external thread is screwed through the locknut. Once the external thread has passed through the locknut, the cone screw is held, on the one hand, displaceably but, on the other hand, captive in the locknut. When the locknut is placed onto the threaded sleeve, the external thread of the cone screw lies in the portion of the threaded sleeve which, as provided by the invention, is free of threads.

The invention accomplishes that the cone screw will not inadvertently fall out of the threaded sleeve. If several screw elements are employed, it is possible to simultaneously put on several locknuts.

BRIEF DESCRIPTION OF THE DRAWING

One embodiment of the invention is illustrated in th drawing and will be described in greater detail below. It is shown, in an enlarged illustration, in.

BEST MODE OF IMPLEMENTATION OF THE INVENTION

Figure 1:
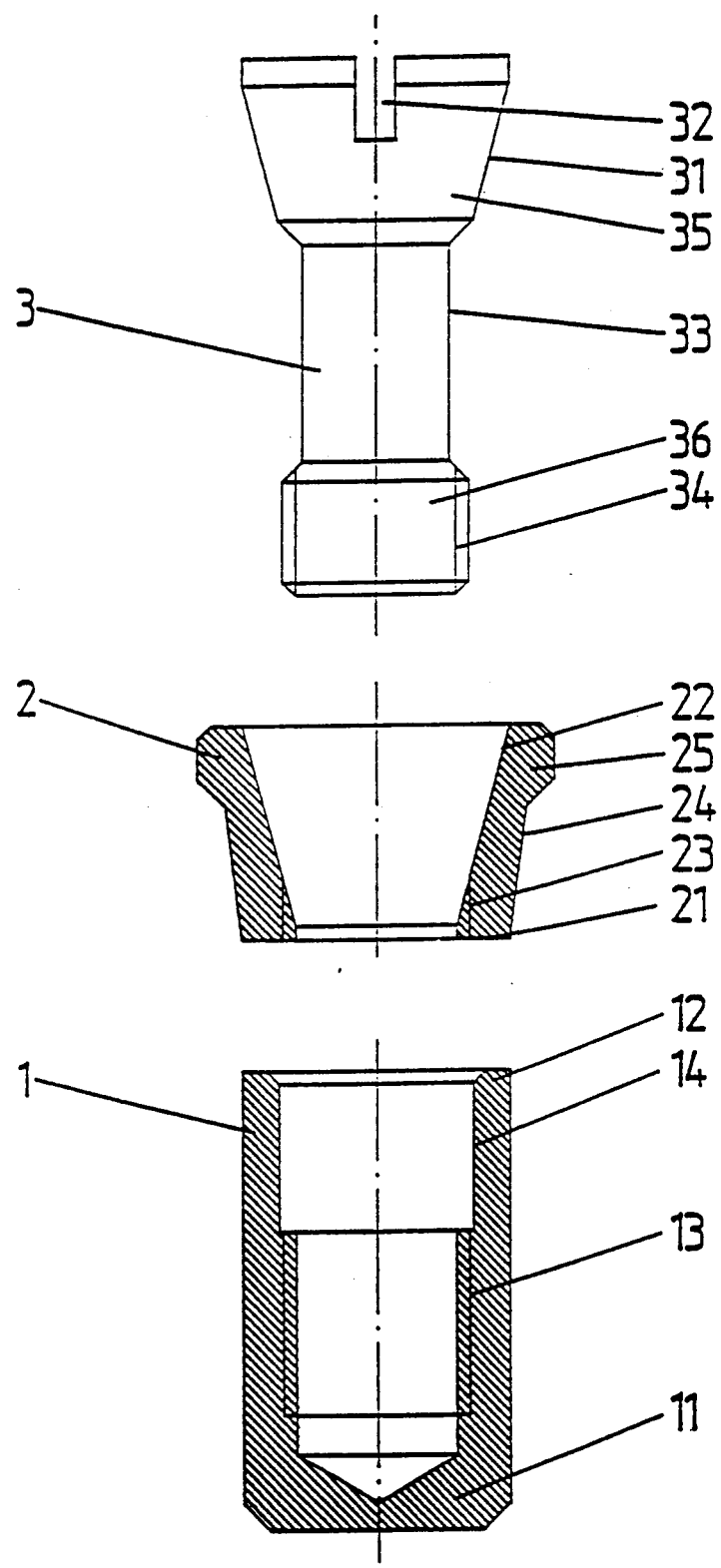
FIG. 1, an axial sectional view of a screw element in the non-mounted state.
Figure 2:
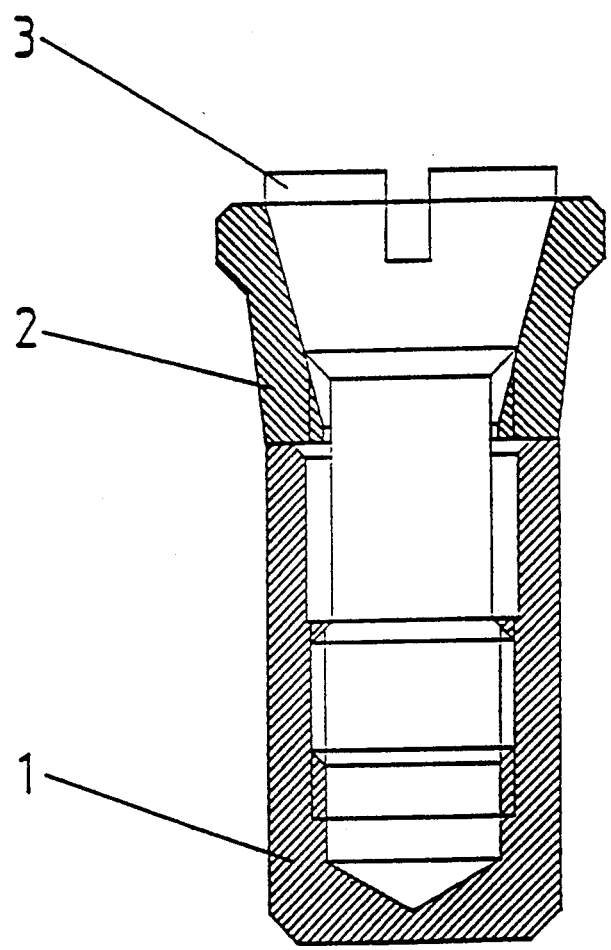
FIG. 2, the screw element shown in FIG. 1 in the mounted state.

The screw element selected as the exemplary embodiment includes a threaded sleeve 1. A locknut 2 is in contact with one end face of threaded sleeve 1. Threaded sleeve 1 and locknut 2 are held in contact with one another by a cone screw 3 that is screwed into threaded sleeve 1 and is supported at locknut 2.

Threaded sleeve 1 is essentially configured as a hollow cylinder. At one end, it is closed by a bottom 11, at the opposite end, its edge 12, it is open. At a distance from bottom 11, threaded sleeve 1 is provided with an internal thread 13. The internal thread is guided only over part of the interior wall of threaded sleeve 1. A portion 14 without thread follows internal thread 13 up to edge 12.

The lower end face 21 of locknut 2 is in contact with the edge 12 of threaded sleeve 1. Locknut 2 has an internal cone 22 which tapers toward threaded sleeve 1. I the region of its smallest diameter, locknut 2 is provided with an internal thread 23. Toward the exterior, locknut 2 is also configured as an external cone 24 which changes, on the side facing away from threaded sleeve 1, into an edge bead 25.

Cone screw 3 has a head 35 that is provided with an external cone 31. External cone 31 is adapted to the internal cone 22 of locknut 2. Moreover, the head 35 of cone screw 3 is provided with a slot 32 to accommodate a screwing tool. In the portion 33 following head 35, cone screw 3 is configured without a thread. At its end opposite external cone 31, cone screw 3 is provided with a threaded shaft 36 having an external thread 34. External thread 34 is adapted to the internal thread 23 of locknut 2 and to the internal thread 13 of sleeve 1.

By means of its external thread 34, cone screw 3 is initially screwed through the internal thread 23 of locknut 2. Once the entire threaded shaft 36 has passed through locknut 2, cone screw 3 can be moved in the axial direction within locknut 2. However, cone screw 3 is held captive in locknut 2. Once the lower end face 21 of locknut 2 has been placed onto the edge 12 of threaded sleeve 1, the threaded shaft 36 of cone screw 3 is disposed in the portion 14 of threaded sleeve 1 that is free of threads. To connect the components of the screw element and thus the components of a dental prosthesis, it is merely necessary to screw the thread 34 of cone screw 3 into the internal thread 13 of threaded sleeve 1 until the external cone 31 of cone screw 3 lies against the internal cone 22 of locknut 2. The components of the multi-part dental prosthesis are then connected with one another.

The multi-part dental prosthesis may be, for example, a divided bridge or an implant superstructure. Threaded sleeve 1 is attached to a crown to be cemented in or to a positioned implant. Locknut 2 is a component of a conditionally removable dental prosthesis or bridge element. Threaded sleeve 1 and locknut 2 are preferably composed of a castable alloy, for example of platinum and iridium.

COMMERCIAL UTILITY

The invention can be employed commercially in the field of dental prosthetics.

I claim:
1. A screw element for connecting a multi-part dental prosthesis, comprising:
   (a) a hollow sleeve having
     (1) a terminal edge surrounding an open end of the sleeve;
     (2) a first, internally threadless length portion extending from said end;
     (3) a second length portion adjoining said first length portion and being remote from said open end;
     (4) a thread provided in said second length portion;
   (b) a locknut being separate from said hollow sleeve; said locknut having
     (1) opposite first and second open ends;
     (2) a passage extending from said first to said second open end and having a conical wall tapering towards said second open end;
     (3) a thread provided in said conical wall along a length portion thereof in a zone of said second end; and
     (4) a terminal edge defining said second open end; and
   (c) a screw having
     (1) a screw head provided with a conical outer wall for complementally fitting into the conical wall of said locknut;
     (2) a first, threadless length portion extending from said screw head;
     (3) a second length portion adjoining said first length portion of said screw and being remote from said screw head; and
     (4) a thread provided in said second length portion of said screw; said thread of said screw matching with said thread of said locknut and with the thread of said sleeve; in an untightened state in which said thread of said screw has passed beyond said thread of said locknut, said screw is slidable in and is held captive by said locknut between said second length portion of said screw and said screw head; and in a tightened state said thread of said screw is in a threaded engagement with said thread of said sleeve, and said conical wall of said screw head is in engagement with said conical wall of said locknut and said terminal edge of said locknut is pressured against said terminal edge of said sleeve.

* * * * *